United States Patent [19]

Kammerer et al.

[11] Patent Number: 5,397,332
[45] Date of Patent: Mar. 14, 1995

[54] SURGICAL MESH APPLICATOR

[75] Inventors: Gene W. Kammerer, East Brunswick, N.J.; M. Joshua Tolkoff, Brookline, Mass.; Robert C. Allman, Wakefield, Mass.; George R. Muise, Stow, Mass.

[73] Assignee: Ethicon, Inc., Somerville, N.J.

[21] Appl. No.: 116,160

[22] Filed: Sep. 2, 1993

[51] Int. Cl.⁶ .............................................. A61B 17/00
[52] U.S. Cl. ..................... 606/151; 604/14; 606/198
[58] Field of Search ............... 606/151, 198; 604/105, 604/106, 107, 14–16, 271

[56] References Cited

U.S. PATENT DOCUMENTS

| | | |
|---|---|---|
| 1,878,671 | 9/1932 | Cantor . |
| 2,067,031 | 1/1937 | Wappler . |
| 3,857,395 | 12/1974 | Johnson et al. . |
| 4,411,655 | 10/1983 | Schreck .................. 604/104 X |
| 4,590,938 | 5/1986 | Segura et al. . |
| 4,654,028 | 3/1987 | Suma . |
| 4,655,219 | 4/1987 | Petruzzi . |
| 4,705,041 | 11/1987 | Kim . |
| 4,909,789 | 3/1990 | Taguchi et al. . |
| 4,935,006 | 6/1990 | Hasson .................. 604/268 X |
| 5,113,846 | 5/1992 | Hildebrandt et al. ........ 604/105 X |
| 5,116,357 | 5/1992 | Eberbach ................ 606/213 |
| 5,122,155 | 6/1992 | Eberbach ................ 606/213 |
| 5,141,515 | 8/1992 | Eberbach ................ 606/110 |
| 5,267,554 | 12/1993 | Wilk .................... 606/198 |
| 5,280,782 | 1/1994 | Wilk .................... 606/198 |
| 5,304,187 | 4/1994 | Green et al. ............. 606/151 |

Primary Examiner—Stephen C. Pellegrino
Assistant Examiner—Nancy Mulcare

[57] ABSTRACT

An applicator for applying a sheet of surgical material, e.g., a surgical mesh, to internal body tissue includes a delivery tube, a deployment tube slidably received within the delivery tube, and a shaft or irrigation tube slidably received within the deployment tube. An expandable spreader tip is connected between the distal ends of the shaft and the deployment tube. The spreader tip is collapsed and inserted in the delivery tube with the surgical mesh. The applicator is inserted through a trocar tube into a body cavity and the spreader tip is exposed by retracting the delivery tube relative to the deployment tube and shaft. The applicator has a first actuator for urging the spreader tip and surgical mesh into engagement with the tissue as the deployment tube is retracted and a second actuator for advancing the deployment tube relative to the shaft to expand the spreader tip to apply the surgical mesh to the tissue. The spreader tip includes a plurality of flexible strips each having its opposite ends pivotally connected to the distal ends of the shaft and the deployment tube. The applicator includes a return spring to bias the deployment tube proximally relative to the shaft to normally maintain the spreader tip collapsed.

40 Claims, 10 Drawing Sheets

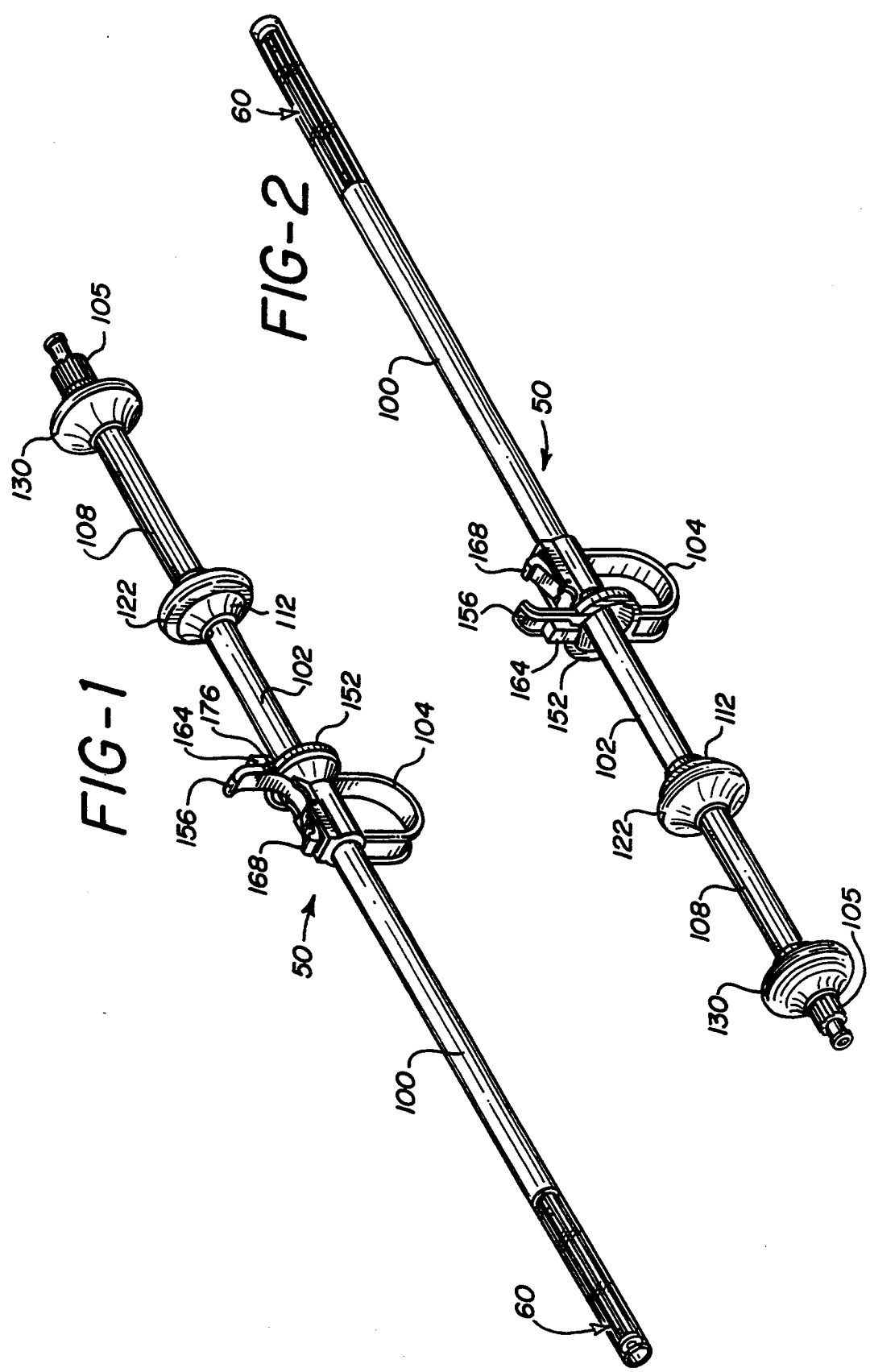

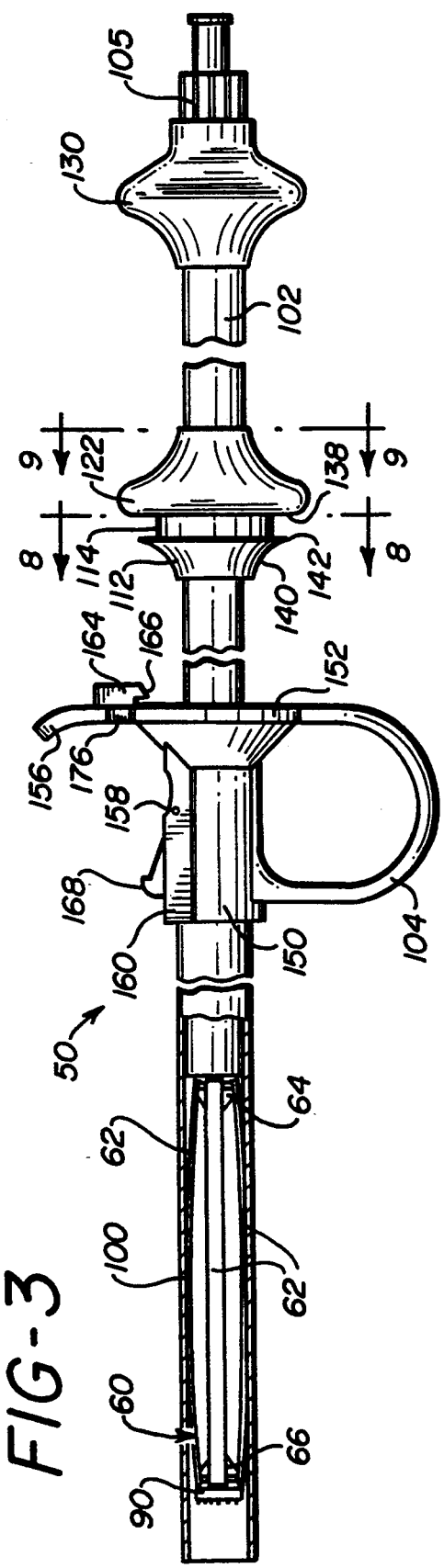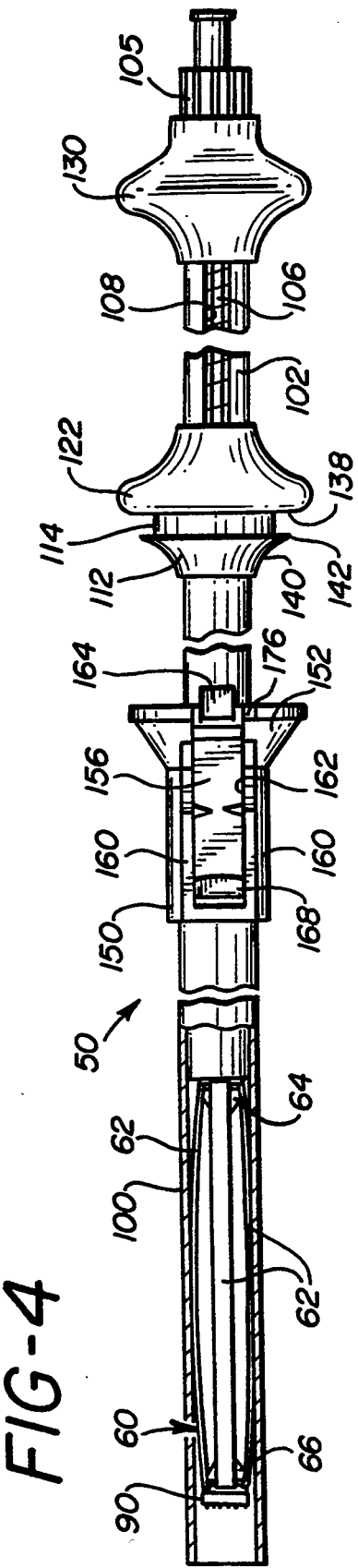

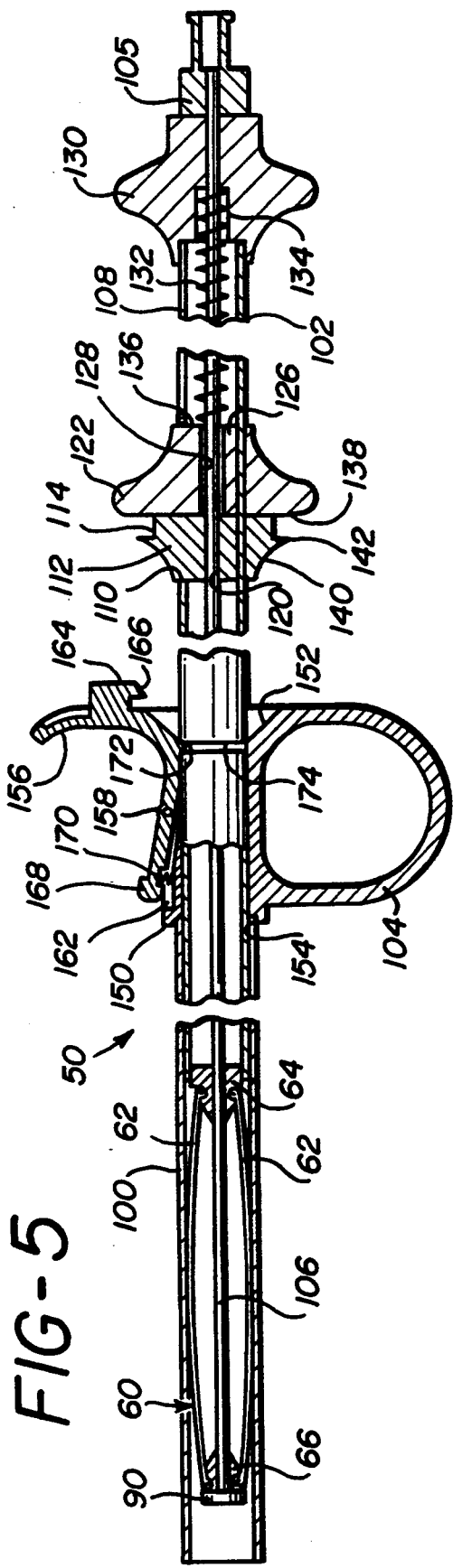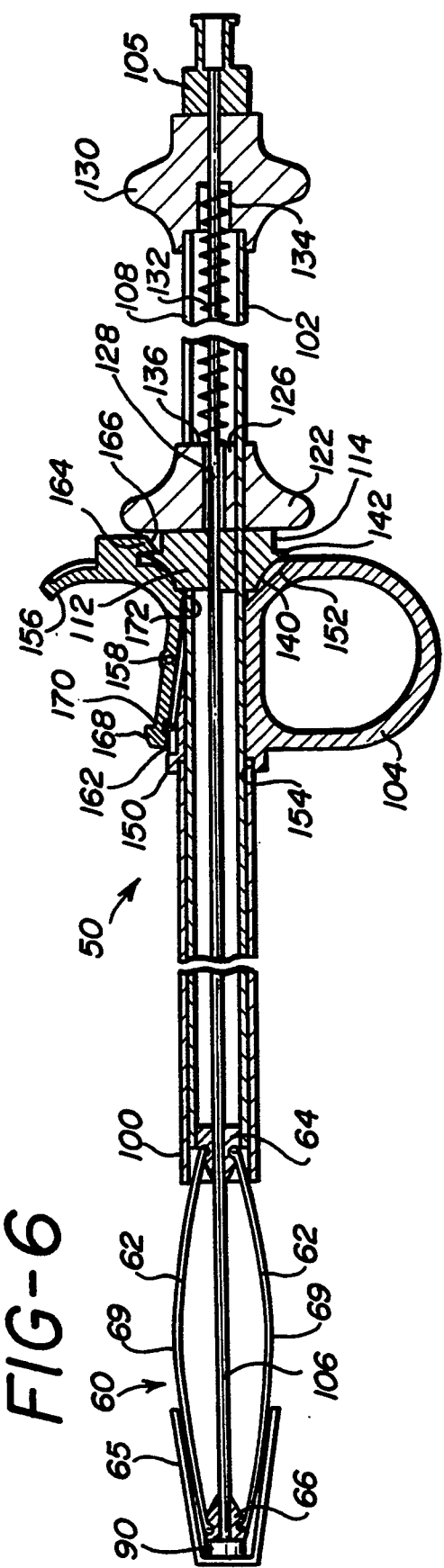

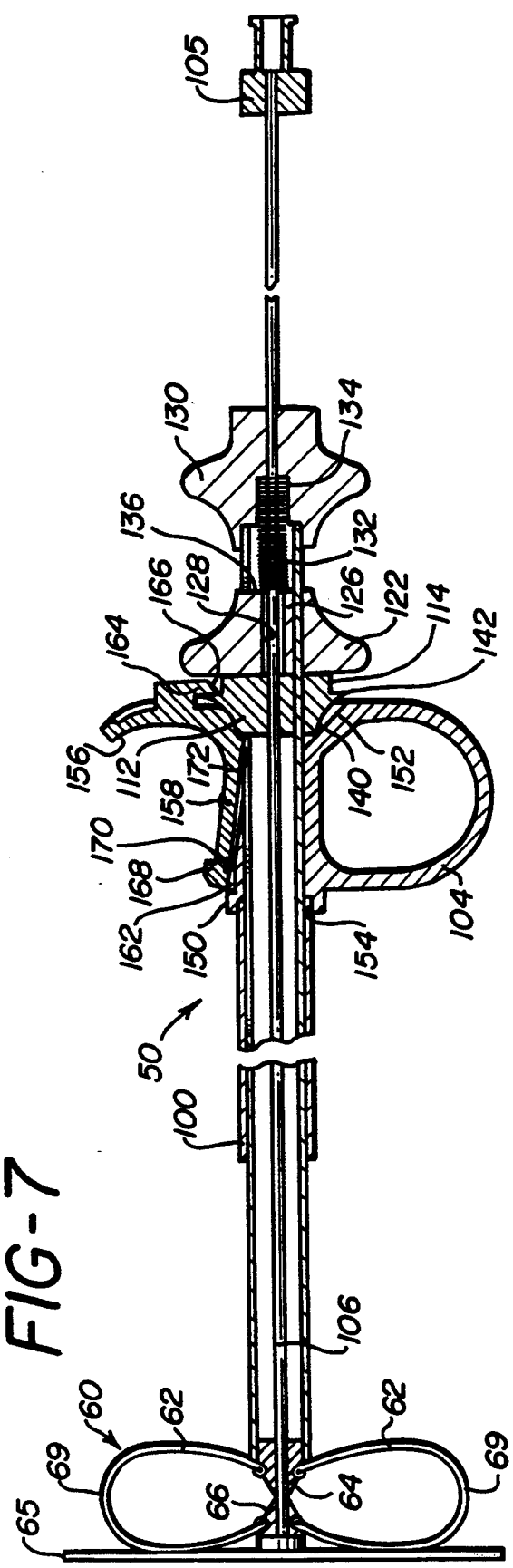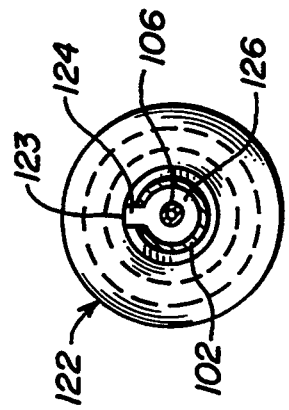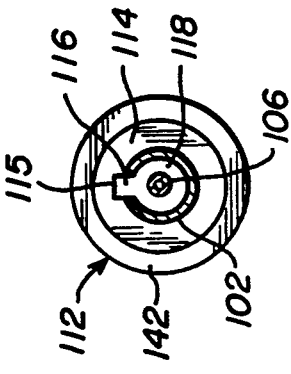

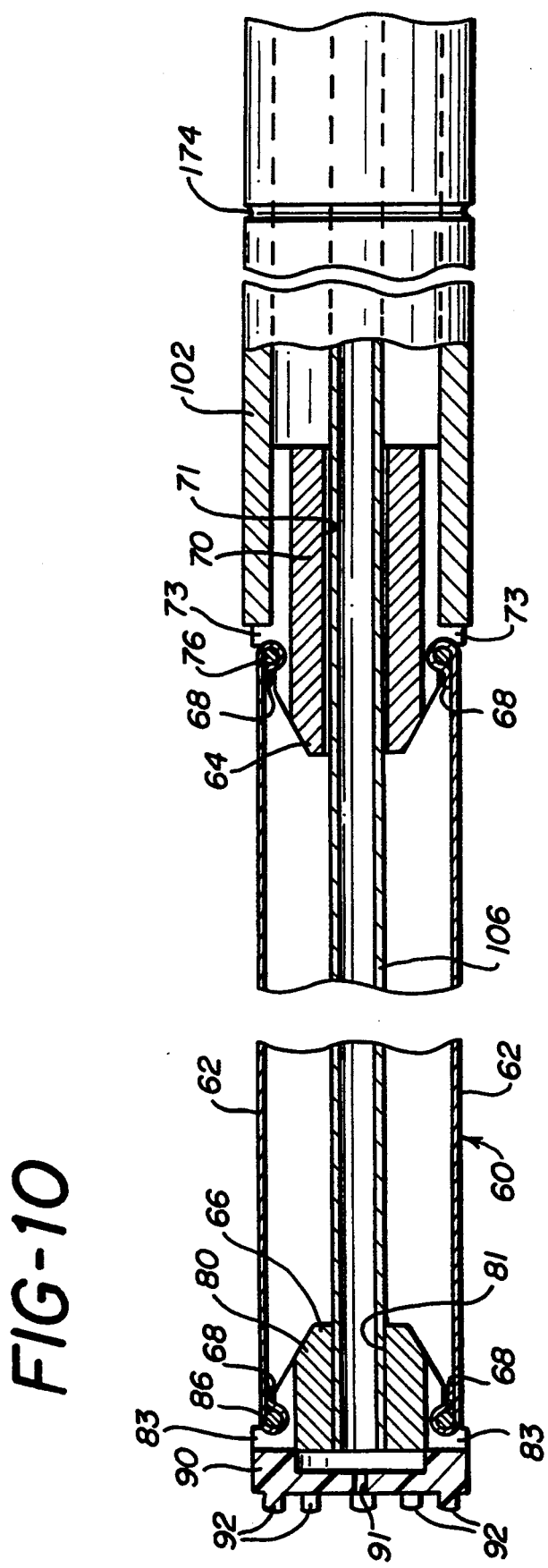

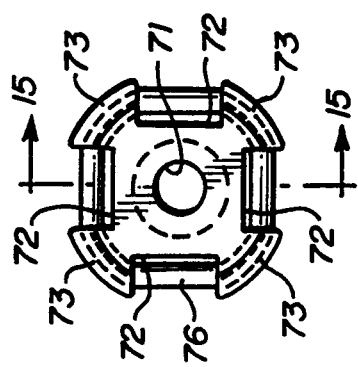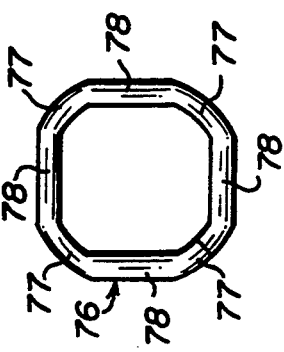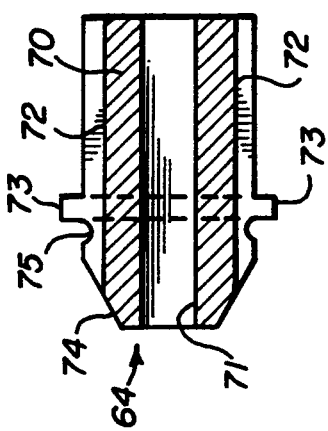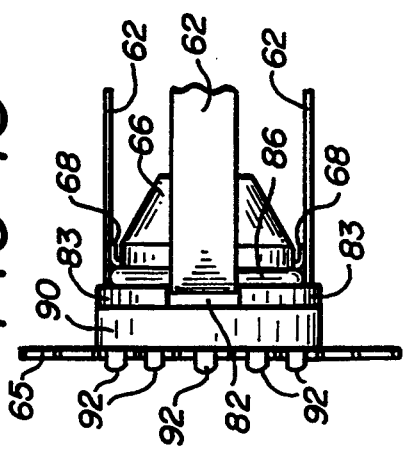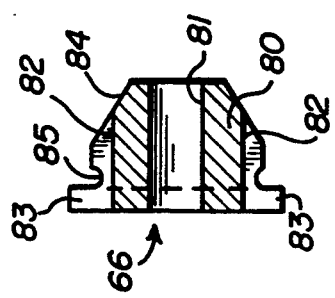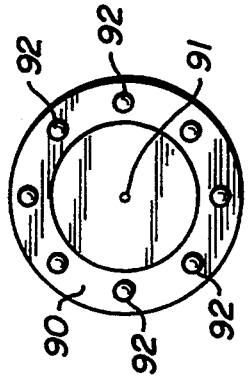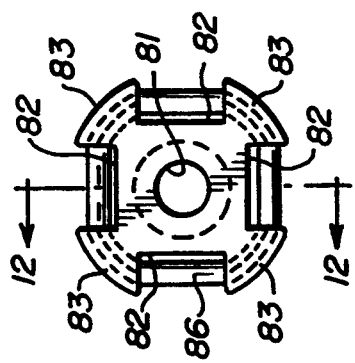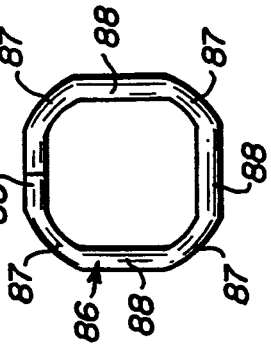

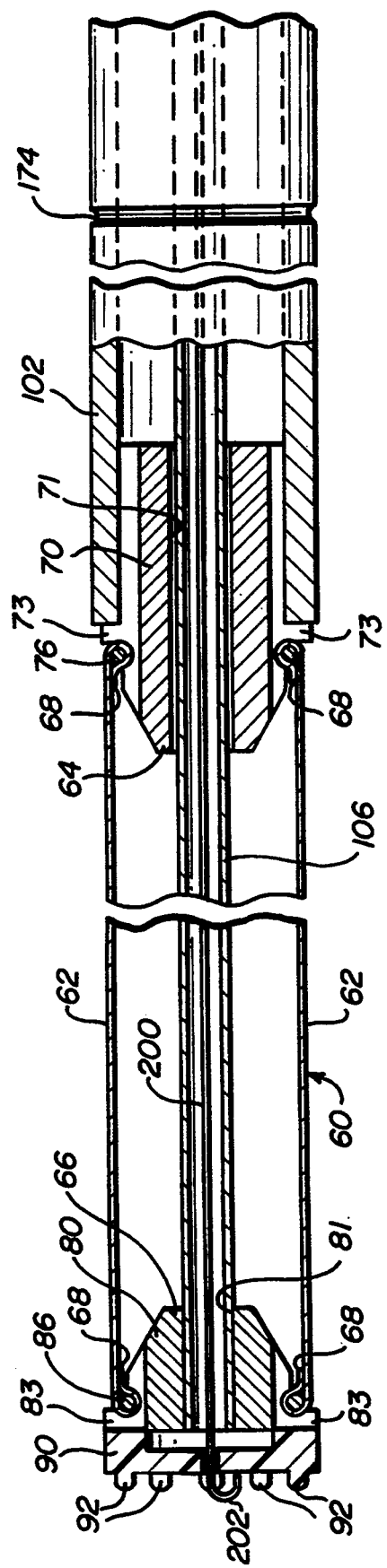

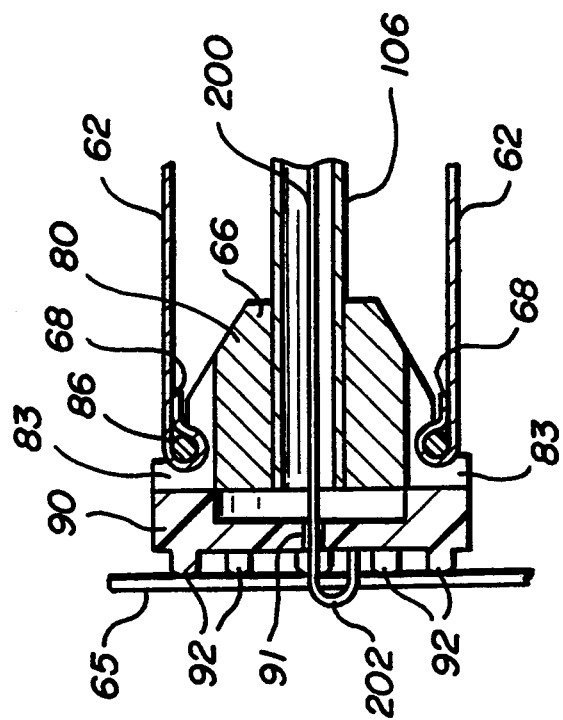
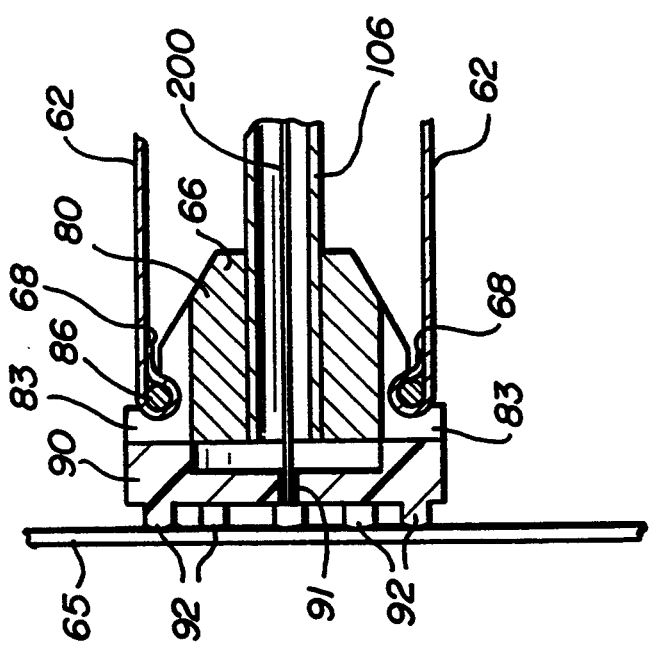

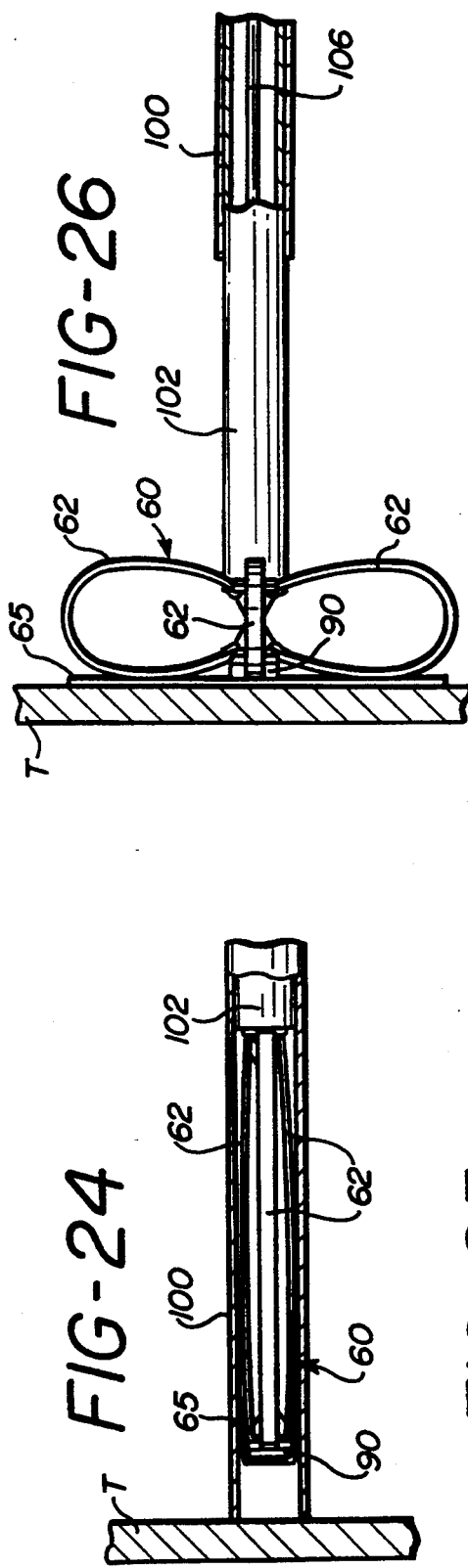
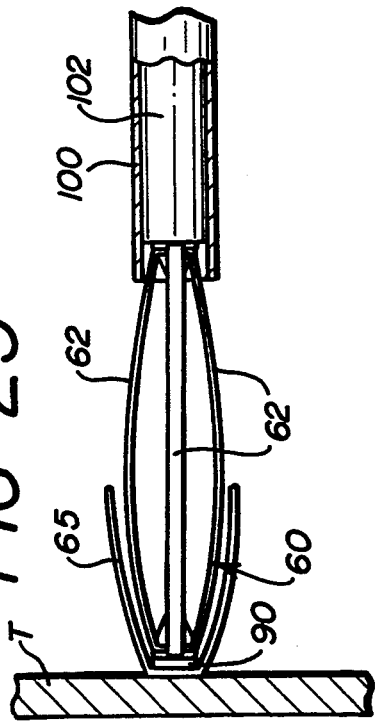
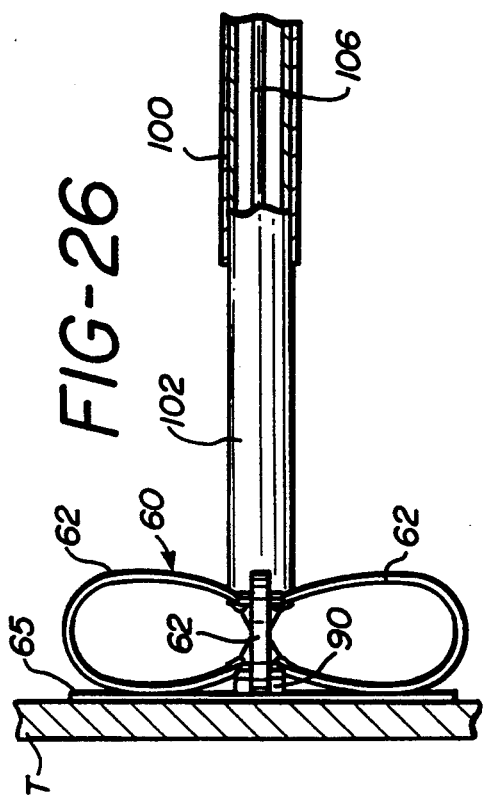
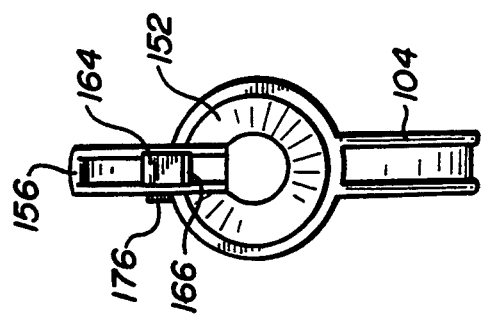
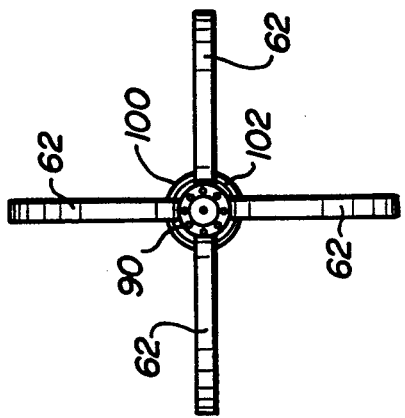

SURGICAL MESH APPLICATOR

FIELD OF THE INVENTION

The present invention relates to an applicator adapted for applying a sheet of surgical material such as a surgical mesh to tissue within a human body and, more particularly, to a surgical mesh applicator including an expandable spreader tip which is insertable into the body through an incision to enable a surgeon to apply a surgical mesh to tissue inside the body. The applicator is particularly suitable for insertion through an endoscopic tube for spreading a surgical mesh over internal body tissue in the performance of surgery to repair a hernia.

BACKGROUND OF THE INVENTION AND PRIOR ART

In the prior art, it is known to utilize an inserter device for the purpose of installing an absorbant tampon in the internal vaginal cavity. For example, U.S. Pat. No. 3,857,395 discloses an inserter device which includes a pair of outwardly bendable arms which bilaterally spread the tampon within the vaginal cavity.

In addition, other types of instruments are known in the prior art for manipulating internal body tissue. For example, U.S. Pat. No. 4,909,789 discloses observation assisting forceps including a set of expandable wires mounted on a shaft which is normally retracted into a sheath. When the shaft is advanced, the wires project out of the sheath and expand into a fan-shaped configuration in the same plane. The expanded wires can be used to set aside internal organs obstructing the observation with an abdominal cavity endoscope. The wires are provided at the tips with spherical members which prevent the organs from being hurt.

U.S. Pat. No. 4,654,028 discloses an incision opening expansion holder including a plurality of wires at the end of an inner tube which are three dimensionally expanded when projecting out of an outer tube to expand an incision of a blood vessel graft for purposes of inosculation. U.S. Pat. No. 4,705,041 discloses a tissue dilator comprising a catheter which supports an expandable member, e.g., a balloon or a scissor-like member. U.S. Pat. No. 1,878,671 discloses a dilator for opening a body cavity including an ovate head mounted on a wire received in a tube which is inserted into the body cavity. U.S. Pat. No. 4,655,219 discloses a tissue grasping accessory including a plurality of flexible grasping arms for use with an endoscopic instrument to grasp a tissue specimen. U.S. Pat. No. 4,590,938 discloses a device for removal of kidney stones through the working channel of an endoscope including a basket comprising four outwardly bowed, generally flat spring arms which are expandable into a bulbous shape and collapsed when retracted into a sheath. The relatively broad, flat surfaces of the spring strips deflect the kidney tissue surrounding the stone while the distally enlarged volume of the basket allows the surgeon to dislodge and capture the stone.

Co-pending U.S. patent application Ser. No. 779,432, filed Oct. 18, 1991, entitled "Adhesion Barrier Applicator", assigned to the same assignee as the present invention, discloses an applicator for applying a sheet of surgical material, e.g., an absorbable adhesion barrier, to internal body tissue to reduce the incidence of postoperative adhesions. The applicator is insertable into a trocar or endoscopic tube through an incision in a body wall to enable a surgeon to apply the adhesion barrier to tissue inside the body. The applicator includes a set of telescoping tubes comprising an outer delivery tube, an intermediate deployment tube, and an inner irrigation tube. An expandable spreader tip is mounted at the distal end of the irrigation tube and connected to the distal end of the deployment tube. By advancing the deployment tube and irrigation tube relative to the delivery tube, the expandable spreader tip is exposed at the distal end of the delivery tube. The spreader tip is expanded by movement of the deployment tube relative to the irrigation tube to spread the adhesion barrier over the tissue. A nozzle is provided at the distal end of the irrigation tube for applying a saline solution to the adhesion barrier.

The adhesion barrier applicator of U.S. patent application Ser. No. 779,432 is advantageously employed in performing gynecologic-pelvic surgery to apply an adhesion barrier to internal body tissue. The adhesion barrier is applied at the surgical site to the traumatized tissue surfaces after hemostasis to physically separate opposing tissue surfaces during the period of repair or reperitonealization of the tissue. The adhesion barrier applicator is particularly suitable for applying an adhesion barrier of relatively small size to the internal body tissue. The adhesion barrier applicator employs a single stroke actuator mechanism to expose the spreader tip at the distal end of the delivery tube and expand the spreader tip to spread the adhesion barrier over the tissue. During the one-stroke operation of the acutator mechanism, the spreader tip cannot be repositioned on the tissue until the expansion of the spreader tip is completed. Thus, prior to the actuation of the adhesion barrier applicator, the spreader tip must be accurately aligned with the surgical site. Once the operation of the actuator mechanism is initiated, it is difficult to adjust the position of the spreader tip on the tissue. Also, the spreader tip of the adhesion barrier applicator does not incorporate any grasping features to enhance the ability of the spreader tip to adjust the position of the adhesion barrier on the tissue. Further, in the operation of the adhesion barrier applicator, the deployment tube cannot be rotated about its axis relative to the delivery tube to adjust the angular orientation of the spreader tip and the adhesion barrier.

Accordingly, it is an object of the present invention to provide an applicator which is adapted to precisely control the placement of a sheet of surgical material such as a surgical mesh to internal body tissue.

Another object of the invention is to provide an applicator to facilitate the installation of a sheet of surgical material such as a surgical mesh through an endoscopic tube to tissue in a body cavity.

It is also an object of the invention to provide a surgical mesh applicator which is suitable for insertion through an endoscopic tube and is adapted to spread the surgical mesh over a tissue application area to minimize the need for manipulation of the surgical mesh by separate grasping instruments.

A further object of the invention is to provide a surgical mesh applicator including an expandable spreader tip which is rotatable when retracted into the delivery tube and when exposed from the delivery tube to allow the angular orientation of the surgical mesh to be adjusted.

It is a further object of the invention to provide a surgical mesh applicator including an expandable spreader tip which is adapted to grip the surgical mesh to facilitate the placement of the surgical mesh in a desired position on the tissue.

SUMMARY OF THE INVENTION

The present invention achieves an applicator which is adapted for insertion through a trocar or endoscopic tube to apply a sheet of surgical material such as a surgical mesh to internal body tissue. The applicator can also be used to apply other types of fabrics used in surgery, e.g., topical hemostats, adhesion barriers and surgical patches.

The invention is embodied in an applicator for applying a spreadable sheet of surgical material to internal body tissue comprising a delivery tube, a deployment tube slidably received within the delivery tube, and a shaft slidably received within the deployment tube with a distal end of the shaft projecting from the distal end of the deployment tube. An expandable spreader tip is mounted at the distal end of the shaft and connected to the distal end of the deployment tube for spreading the sheet of surgical material over the tissue. The spreader tip is collapsed when inserted in the delivery tube with the surgical material. The applicator includes means for retracting the delivery tube relative to the deployment tube and the shaft to expose the spreader tip and the surgical material at the distal end of the delivery tube. The applicator includes first actuator means for urging the spreader tip and the surgical material into engagement with the tissue as the deployment tube is retracted and second actuator means for advancing the deployment tube relative to the shaft to expand the spreader tip to apply the surgical material to the tissue. Preferably, a return spring is provided for biasing the deployment tube in the proximal direction relative to the shaft to normally maintain the spreader tip collapsed.

In accordance with one aspect of the present invention, the spreader tip comprises a plurality of flexible strips each pivotally connected at its opposite ends to the distal end of the shaft and to the distal end of the deployment tube. The strips are flexed outwardly when the deployment tube is advanced relative to the shaft to spread the surgical material over the tissue. Each of the flexible strips has an intermediate portion which bulges laterally outward when the strip is flexed for spreading the surgical material over the tissue. Preferably, the strips are spaced circumferentially apart about the spreader tip. When the spreader tip is actuated, the strips flex laterally outward into a convex shape to spread the surgical material over the tissue.

A preferred embodiment of the spreader tip includes a plurality of distally extending prongs for engaging the sheet of surgical material to adjust the placement of the surgical material on the tissue. The prongs function as fabric engaging fingers which allow the sheet of surgical material to be displaced and rotated by movement of the spreader tip over the tissue.

In accordance with another aspect of the invention, the deployment tube and shaft of the applicator are rotatable together relative to the delivery tube to adjust the angular orientation of the spreader tip and the surgical material. Thus, the spreader tip is rotatable when retracted inside the delivery tube and when exposed at the distal end of the delivery tube to facilitate the desired alignment and placement of the surgical material on the tissue.

A preferred embodiment of the applicator includes latch means for latching the delivery tube in a retracted position with the spreader tip and the surgical material exposed at the distal end of the delivery tube. The latch means is operable in any rotational orientation of the deployment tube relative to the delivery tube to latch the delivery tube in the retracted position. The latch means is adapted to permit rotation of the deployment tube and the shaft relative to the delivery tube with the delivery tube latched in the retracted position. Preferably, the latch means comprises a latching member on the delivery tube and a latch ring on the deployment tube adapted to engage the latching member in any rotational orientation of the deployment tube relative to the delivery tube when the delivery tube is moved to the retracted position. The latching member and latch ring permit the spreader tip to be disposed in any desired angular orientation when it is exposed at the distal end of the delivery tube.

In accordance with another aspect of the invention, the application includes detent means for releasably engaging the deployment tube to retain the spreader tip inside the delivery tube prior to the exposure of the spreader tip from the distal end of the delivery tube. The detent means is operable in any rotational orientation of the deployment tube relative to the delivery tube to retain the spreader tip inside the delivery tube. The detent means is adapted to permit rotation of the deployment tube and shaft relative to the delivery tube with the spreader tip retracted inside the delivery tube. Preferably, the detent means comprises a latching member on the delivery tube and an annular groove on the deployment tube adapted to engage the latching member in any rotational orientation of the deployment tube relative to the delivery tube when the spreader tip is retracted.

In a preferred embodiment of the applicator, a hollow funnel-shaped flange is provided at the proximal end of the delivery tube for guiding the spreader tip and the surgical material into the delivery tube. The shaft comprises an irrigation tube for supplying fluid, e.g., a saline solution, to the sheet of surgical material. A nozzle is provided at the distal end of the irrigation tube for discharging the fluid therefrom. Preferably, the nozzle includes a plurality of distally extending prongs for engaging the sheet of surgical material to adjust the placement of the surgical material on the tissue.

In another embodiment of the applicator, a pickup mechanism is provided for securing the sheet of surgical material to the spreader tip. The pickup mechanism comprises a wire slidably mounted on the spreader tip and provided with a hook for engaging the surgical material. The hook is adapted to snare the sheet of surgical material on the spreader tip to allow the sheet to be picked up and maneuvered into a desired position. The hook is located at the distal end of the wire and can be controlled from the proximal end of the applicator so that the hook can be extended from or retracted into the spreader tip.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a front perspective view of the first embodiment of a surgical mesh applicator constructed in accordance with this invention;

FIG. 2 is a rear perspective view of the surgical mesh applicator of FIG. 1;

FIG. 3 is a partially cutaway side elevation of the surgical mesh applicator of FIG. 1;

FIG. 4 is a partially cutaway top view of the surgical mesh applicator of FIG. 3;

FIG. 5 is a longitudinal section of the surgical mesh applicator of FIG. 3;

FIG. 6 is a longitudinal section of the surgical mesh applicator of FIG. 3 showing the spreader tip exposed;

FIG. 7 is a longitudinal section of the surgical mesh applicator of FIG. 3 showing the spreader tip expanded;

FIG. 8 is a vertical section of the surgical mesh applicator along line 8—8 of FIG. 3;

FIG. 9 is a vertical section of the surgical mesh applicator along line 9—9 of FIG. 3;

FIG. 10 is an enlarged, partially cutaway longitudinal section showing the spreader tip and nozzle of the surgical mesh applicator;

FIG. 11 is a distal end view of a retainer member and pivot ring at the distal end of the spreader tip;

FIG. 12 is a longitudinal section of the retainer member along line 12—12 of FIG. 11;

FIG. 13 is an end view of the pivot ring of FIG. 11;

FIG. 14 is a proximal end view of a retainer member and pivot ring at the proximal end of the spreader tip;

FIG. 15 is a longitudinal section of the retainer member along line 15—15 of FIG. 14;

FIG. 16 is an end view of the pivot ring of FIG. 14;

FIG. 17 is a distal end view of the nozzle at the distal end of the spreader tip;

FIG. 18 shows the nozzle of the spreader tip engaged with a surgical mesh;

FIG. 19 shows a modified embodiment of the surgical mesh applicator of the present invention;

FIGS. 20 and 21 illustrate the operation of the modified embodiment of FIG. 19;

FIGS. 24–26 are fragmentary views which illustrate the operation of the spreader tip of the surgical mesh applicator of FIG. 3;

FIG. 27 is a distal end view of the expanded spreader tip; and

FIG. 28 is a proximal end view of a finger grip on the surgical mesh applicator of FIG. 3.

DETAILED DESCRIPTION OF PREFERRED EMBODIMENTS

Figure 22:
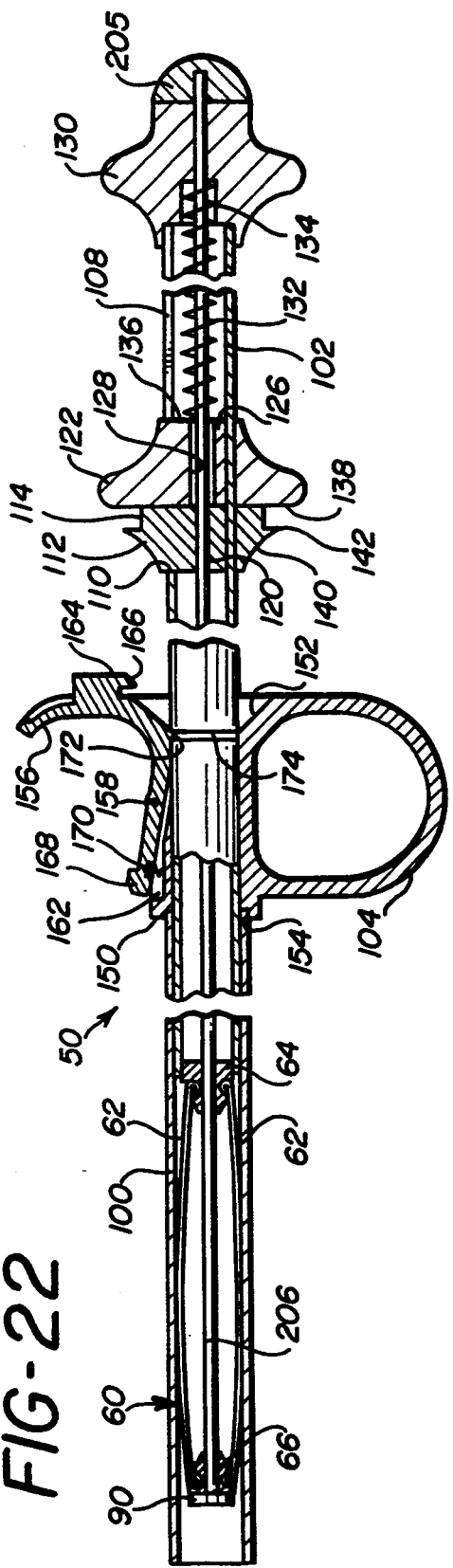
FIG. 22 shows a further embodiment of the surgical mesh applicator of the present invention.

Referring to FIG. 1, the present invention is embodied in an applicator or delivery device, generally 50, including an expandable spreader tip 60 which is insertable through an incision or a natural body orifice to enable a surgeon to apply a sheet 65 (FIG. 6) of surgical material, such as a surgical mesh or an adhesion barrier, to tissue inside the body. The applicator 50 is particularly suitable for use by a surgeon to apply the surgical mesh 65 to internal body tissue at a site where a surgical repair, e.g., a hernia operation, is to be performed. The surgical mesh 65 can be made of a material such as rayon which has a tendency to stick to the internal body tissue or a non-wetting material such as polypropylene.

As shown in FIG. 1, the surgical mesh applicator 50 includes a pair of elongated tubes 100 and 102 which are telescoped together for longitudinal movement relative to each other. Preferably, the outer tube 100 consists of clear plastic material and, if desired, the tube 102 is made of the same material. The outer tube 100 is secured at its proximal end to a finger grip 104. The outer tube 100 constitutes a delivery tube through which the spreader tip 60 and the surgical mesh 65 is inserted into the body. The inner tube 102 is slidably received by the outer delivery tube 100 and is freely rotatable about the longitudinal axis of the delivery tube 100. The inner tube 102 serves as a deployment tube for actuating the spreader tip 60 and applying the surgical mesh 65 to internal body tissue.

Inside the deployment tube 102 is an elongated shaft or push rod 106 (FIG. 5) which projects beyond the distal end of the deployment tube 102 and supports the expandable spreader tip 60. The deployment tube 102 is slidable longitudinally relative to the push rod 106 to expand the spreader tip 60 to spread the surgical mesh 65 over the internal body tissue. Preferably, the push rod 106 is a hollow shaft and serves as an irrigation tube for supplying fluid to the surgical mesh 65. For example, the push rod 106 is made of metal, such as stainless steel.

A fluid coupling member 105 for connection to a source of fluid (not shown) is attached to the proximal end of the hollow push rod 106. For example, the fluid coupling member 105 consists of a hollow cylindrical element made of plastic and known as a "Luer Lok" which is adapted to receive a syringe or a compressible bulb for supplying fluid via the hollow push rod 106 to the spreader tip 60.

The deployment tube 102 has a longitudinal slot 108 (FIG. 4) extending distally for a predetermined length from the proximal end of the tube 102. The longitudinal slot 108 terminates at a distal edge 110 (FIG. 5). A latch ring 112 is slidably mounted on the deployment tube 102 and is slidably received in the longitudinal slot 108 for movement therealong relative to the deployment tube 102. As shown in FIG. 8, the latch ring 112 comprises a hollow cylindrical wall 114 including a longitudinal notch 115. A depending flange 116 is secured in the notch 115 and is slidably received in the longitudinal slot 108 of the deployment tube 102. The depending flange 116 supports an inner cylindrical member 118 which is slidably received inside the deployment tube 102. The cylindrical member 118 has an axial bore 120 (FIG. 5) in which the push rod 106 is secured.

A first actuator member comprising an annular delivery flange 122 is slidably mounted on the deployment tube 102. The annular delivery flange 122 is slidably received in the longitudinal slot 108 for movement therealong relative to the deployment tube 102. As shown in FIG. 9, the delivery flange 122 includes a longitudinal notch 123 in which a depending flange 124 is secured. The depending flange 124 is slidably received in the longitudinal slot 108 of the deployment tube 102. The depending arm 124 supports an inner cylindrical member 126 which is slidably received inside the deployment tube 102. The cylindrical member 126 has an axial bore 128 (FIG. 5) for slidably receiving the push rod 106.

A second actuator member comprising an annular deployment flange 130 is secured to the proximal end of the deployment tube 102. An elongated compression coil spring 132 is mounted on the push rod 106 and interposed between the delivery flange 122 and the deployment flange 130. The proximal end of the compression spring 132 is received in an axial counterbore 134 formed in the deployment flange 130. The distal end of the compression spring 132 is engaged with a flat rear surface 136 on the inner cylindrical member 126 of the delivery flange 122. The delivery flange 122 has a flat front surface 138 which is urged by the compression spring 132 into contact with the rear cylindrical wall 114 of the latch ring 112. The latch ring 112 and the delivery flange 122 are normally biased toward the distal end 110 of the longitudinal slot 108 by the compression coil spring 132. An outwardly tapered collar 140 at the front of the latch ring 112 defines an annular lip 142 for securing the latch ring 112 to the finger grip 104 when the deployment tube 102 is advanced.

As shown in FIG. 3, the finger grip 104 includes a hollow cylindrical body 150 connected to a rear funnel-shaped flange 152 which facilitates the insertion of the spreader tip 60 and the deployment tube 102 into the delivery tube 100. The cylindrical body 150 has a counterbore 154 in which the proximal end of the delivery tube 100 is secured. A latch arm 156 is mounted on a pivot pin 158 which extends transversely between a pair of upstanding longitudinal flanges 160 (FIG. 4) extending along opposite sides at the top of the cylindrical body 150 of the finger grip 104. The latch arm 156 is located in a longitudinal slot 162 (FIG. 5) which extends between the flanges 160 into the funnel-shaped flange 152 and allows the latch arm 156 to engage the deployment tube 102.

As shown in FIG. 5, the latch arm 156 projects upwardly from the finger grip 104 to provide a finger rest for engagement by the index finger of the surgeon. A depending latch finger 164 is provided at the rear of the latch arm 156 for latching the annular lip 142 when the latch ring 112 is advanced into the funnel-shaped flange 152 (FIG. 6) of the finger grip 104. The latch finger 164 has a beveled edge 166 (FIG. 5) which rides along the tapered collar 140 of the latch ring 112 to pivot the latch arm 156 and allow the latch finger 164 to move over and engage the annular lip 142 when the delivery tube 100 is retracted to expose the spreader tip 60 at the distal end of the delivery tube 100. The latch arm 156 has a release lever 168 at its distal end which is biased upwardly from the cylindrical body 150 by a coil spring 170. The annular lip 142 is movable into engagement with the latch finger 164 in any rotational orientation of the deployment 102 relative to the delivery tube 100 to retain the delivery tube 100 in the retracted position. The annular lip 142 permits the deployment tube 102 and the push rod 106 to be rotated relative to the delivery tube 100 with the delivery tube 100 latched in the retracted position to adjust the angular orientation of the spreader tip 60.

A detent 172 is provided on the latch arm 156 for engagement with an annular groove 174 formed in the deployment tube 102 to hold the spreader tip 60 in a retracted position inside the distal end of the delivery tube 100. The annular groove 174 is engageable by the detent 172 in any rotational orientation of the deployment tube 102 relative to the delivery tube 100 to retain the spreader tip 60 inside the delivery tube 100. Also, the annular groove 174 permits the deployment tube 102 and the push rod 106 to be rotated relative to the delivery tube 100 with the delivery tube 100 latched in the retracted position to adjust the rotational or angular orientation of the spreader tip 60. On one side of the latch arm 156 is a stop 176 (FIG. 28) which is biased into engagement with the funnel-shaped flange 152 when the deployment tube 102 is removed from the delivery tube 100 to limit the pivotal movement of the latch arm 156 by the coil spring 170.

Referring to FIG. 3, the spreader tip 60 comprises an expandable basket-like frame made of flexible material, e.g., thin strips of stainless steel. The spreader tip 60 has a plurality of flexible frame members or strips 62 of stainless steel extending longitudinally between a first retainer 64 secured to the distal end of the deployment tube 102 and a second retainer 66 secured to the distal end of the shaft or push rod 106. Preferably, each of the flexible strips 62 is pivotally connected at its opposite ends to the retainers 64 and 66. Each end of the flexible stainless steel strips 62 is folded over itself to provide a flap 68 (FIG. 10) which is attached, e.g., by spot welding, to the strip 62. Each flap 68 provides a hinge-like connection for pivotally attaching the opposite ends of the strip 62 to the retainers 64 and 66 at the distal ends of the push rod 106 and the deployment tube 102, respectively.

As shown in FIG. 6, the spreader tip 60 is collapsed with the flexible strips 62 extending generally parallel to the push rod 106 when the proximal retainer 64 is displaced in the proximal direction away from the distal retainer 66. The spreader tip 60 is expanded (FIG. 7) with the flexible strips 62 bulging radially outward when the proximal retainer 64 is displaced in the distal direction toward the distal retainer 66. In the relaxed or collapsed configuration of the spreader tip 60 (FIG. 6), each strip 62 is slightly bent and extends radially outward at its midpoint 69 away from the push rod 106. When the spreader tip 60 is actuated (FIG. 7), the strips 62 are flexed laterally outward into a convex shape to spread the surgical material over the tissue. Preferably, the longitudinal strips 62 are spaced circumferentially about the spreader tip 60 at equal intervals. For example, as shown in FIG. 27, the four strips 62 are spaced apart at intervals of 90 degrees.

As shown in FIG. 10, the proximal retainer 64 has an elongated, hollow body 70 of generally cylindrical shape having an axial bore 71 extending therethrough in which the push rod 106 is slidably received. As shown in FIGS. 14 and 15, the sides of the retainer body 70 are cut away to form four longitudinal channels 72 spaced circumferentially apart by 90 degrees. Also, four radially extending flanges 73 are formed on the retainer body 70 and disposed between the longitudinal channels 72. The flanges 73 engage the distal end of the deployment tube 102 with the retainer 64 inserted therein. The retainer body 70 includes a conically tapered distal end portion 74. Adjacent to the distal side of the flanges 73 is a circumferential groove 75 for receiving a retainer ring 76 to which the proximal ends of the strips 62 are pivotally connected. As shown in FIG. 16, the ring 76 has four rounded corners 77 located in the portions of the groove 75 adjacent to the flanges 73 and four straight portions 78 to which the hinge-like flaps 68 of the strip 62 are pivotally attached.

Referring to FIG. 10, the distal retainer 66 comprises an elongated, hollow body 80 of generally cylindrical shape having an axial bore 81 extending therethrough in which the distal end of the push rod 106 is secured. As shown in FIGS. 11 and 12, the sides of the retainer body 80 are cut away to form four longitudinal channels 82 spaced circumferentially apart by 90 degrees. Also, four radially extending flanges 83 are formed on the retainer body 80 and disposed between the longitudinal channels 82. The retainer body 80 includes a conically tapered distal end portion 84. Adjacent to the proximal side of the flanges 83 is a circumferential groove 85 for receiving a retainer ring 86 to which the distal ends of the strips 62 are pivotally connected. As shown in FIG. 13, the ring 86 has four rounded corners 87 located in the portions of the groove 85 adjacent to the flanges 83 and four straight portions 88 to which the hinge-like flaps 68 of the strip 62 are pivotally attached.

As shown in FIG. 10, a tissue manipulating nozzle or pad 90 is provided at the distal end of the spreader tip 60. Preferably, the pad 90 is generally cylindrical in shape and constructed from a soft pliable material, e.g., a polymeric material such as silicon, urethane or a latex, or a rubber material. The cylindrical pad 90 is adhered to the front face of the distal retainer 66 and provided with a central opening or port 91 through which a saline solution can be applied to the sheet of surgical material 65.

The cylindrical pad 90 includes a series of circumferentially spaced, distally projecting protuberances or prongs 92 formed on its front face. Preferably, the prongs 92 are cylindrical in shape and provided with rounded or pointed tips for engaging the surgical material. The prongs 92 serve as fabric engaging fingers which allow the sheet of surgical material 65 to be displaced and rotated by manipulation of the spreader tip 60. Because of the soft pliable material of the pad 90, the prongs 92 grasp the surgical mesh or other material with sufficient friction to enable the surgical mesh to be moved over the internal body tissue by manipulation of the instrument 50. Also, in the case of a surgical mesh 65 with large size openings or holes (FIG. 18), the prongs 92 fit inside the holes of the mesh 65 to enhance the fabric grasping action of the prongs 92. By appropriate manipulation of the instrument 50, the surgical mesh 65 can be rotated or slid across the internal body tissue to adjust the desired position of the mesh 65 on the tissue.

In the preferred embodiment of the surgical mesh applicator 50, the delivery tube 100 and the deployment tube 102 consist of plastic material and the shaft or push rod 106 is made of stainless steel. The flexible strips 62, the retainers 64 and 66, and the retainer rings 76 and 86 of the spreader tip 60 are also made of stainless steel. The finger grip 104 and the latch arm 156 are made of plastic material. Also, the latch ring 112, the delivery flange 122 and the deployment flange 130 are made of plastic material.

Figure 23:
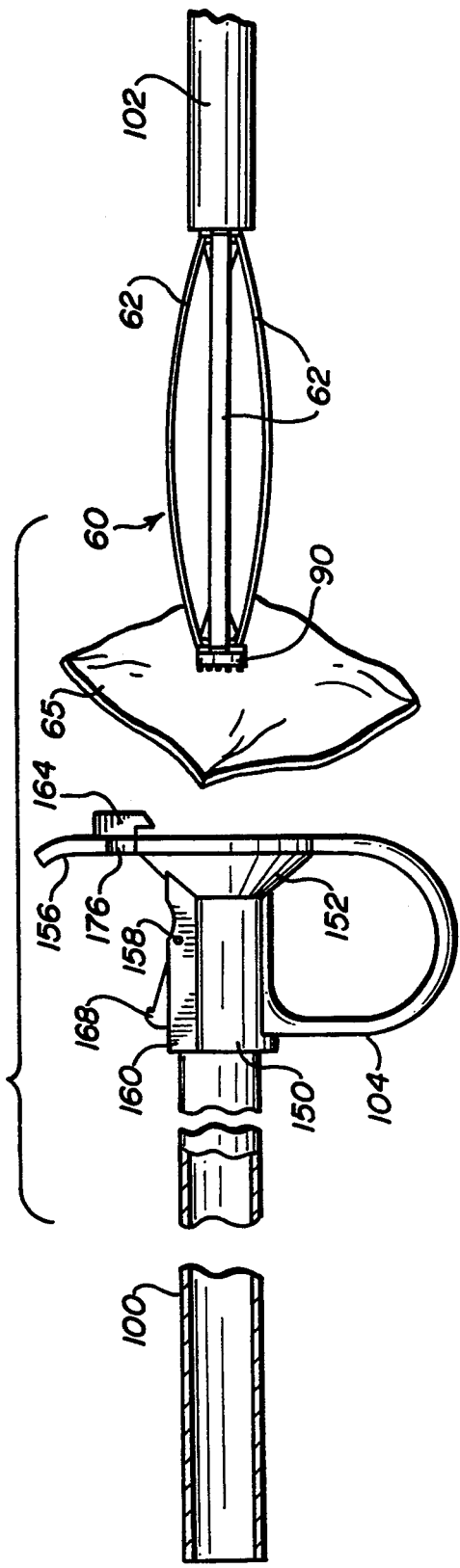
FIG. 23 is a partially cutaway side view illustrating the insertion of a surgical mesh into the applicator of FIG. 3.

In the operation of the surgical applicator 50, the deployment tube 102 is removed from the delivery tube 100 and a sheet of surgical mesh 65 is centered over the mouth of the funnel-shaped flange 152 (FIG. 23). The deployment tube 102 is aligned longitudinally with the delivery tube 100 and the collapsed spreader tip 60 is positioned adjacent to the surgical mesh 65 and pointed toward the funnel-shaped flange 152. The fluid coupling member 105 (or delivery button) and the deployment flange 130 are held together by the thumb and two fingers, respectively, so that the flexible strips 62 of the spreader tip 60 remain in the collapsed condition. The push rod 106 and the deployment tube 102 are advanced distally through the funnel-shaped flange 152 into the delivery tube 100. The surgical mesh 65 is pushed into the delivery tube 100 and folded over the spreader tip 60 by the funnel-shaped flange 152. The spreader tip 60 and surgical mesh 65 are advanced distally by sliding the deployment tube 102 and the push rod 106 along the delivery tube 100 until the spreader tip 60 is stopped in a retracted position (FIG. 5) inside the distal end of the delivery tube 100 by the engagement of the detent 172 on the latch arm 156 with the annular groove 174 in the deployment tube 102.

Next, the surgical instrument 50 is introduced into a body cavity by inserting the delivery tube 100 into a trocar tube (not shown) which extends through an incision in the body wall. The distal end of the delivery tube 100 is positioned against the tissue T (FIG. 24) at the site where the surgical mesh 65 is to be applied. Then, by placing one finger through the finger grip 104 and a thumb on the proximal side of the delivery flange 122, the delivery tube 100 is retracted by pulling on the finger grip 104 while counter pressure is applied to the delivery flange 122 to maintain the distal end of the spreader tip 60 at the surgical site. The delivery flange 122 is pressed against the latch ring 112 to urge the deployment tube 102 and the push rod 106 distally as the delivery tube 100 is retracted. When the delivery tube 100 is completely retracted, the latch finger 164 on the latch arm 156 engages the annular lip 142 on the latch ring 112 to latch the delivery tube 100 in its retracted position (FIG. 6) with the spreader tip 60 and the surgical mesh 65 exposed at the distal end of the delivery tube 100. The surgical mesh 65 is held against the tissue T (FIG. 25) by the pressure exerted on the spreader tip 60.

Next, the deployment tube 102 is advanced distally relative to the delivery tube 100 and to the push rod 106 by pushing the deployment flange 130 in the distal direction. The deployment tube 102 is advanced distally until the spreader tip 60 is fully expanded, i.e., with the proximal retainer 64 engaged with the distal retainer 66 and the flexible strips 62 flexed outwardly into the fully expanded configuration (FIG. 7). The outwardly flexed strips 62 of the spreader tip 60 spread the surgical mesh 65 over the tissue T (FIG. 26) at the surgical site. The latch ring 112 and the delivery flange 122 constitute a split actuator which prevents the push rod 106 from being pulled in the proximal direction as the spreader tip 60 is expanded. If any pulling force is applied to the delivery flange 122 when the latch ring 112 is latched by the latch arm 156, the delivery flange 122 merely slides proximally along the slot 108 away from the latch ring 112 without pulling on the push rod 106. Then, while holding the surgical mesh 65 against the tissue T with the expanded spreader tip 60, the surgical mesh 65 is fastened to the tissue T, e.g., by sutures or staples. A saline solution can be applied via the irrigation tube 106 and the nozzle 90 to maintain the surgical mesh 65 in place on the surgical site. Also, the surgical mesh 65 can be repositioned on the tissue T by placement of the nozzle 90 with its prongs 92 engaging the surgical mesh 65 and by sliding or rotating the nozzle 90 on the tissue T.

After the surgical mesh 65 is attached to the tissue T, the deployment flange 130 is released and allowed to return to its proximal position by the coil spring 132. The flexible strips 62 of the spreader tip 60 are collapsed to facilitate the extraction of the surgical instrument 50 from the trocar tube. The surgical instrument 50 is removed by pulling on the finger grip 104 and latch arm 156 to slide the entire instrument 50 out of the trocar tube at one time.

The surgical mesh applicator 50 is adapted for use with a relatively large and thick sheet 65 of surgical mesh. The spreader tip 60 can be used to apply a sheet 65 of surgical material which is rectangular in shape and up to twice as long as the flexible arms 62. When the sheet 65 of surgical material is folded over the spreader tip 60 and inserted into the delivery tube 100, the folded surgical material does not extend beyond the proximal end of the spreader tip 60 so that the possibility of binding of the surgical material between the delivery tube 100 and the deployment tube 102 is avoided. Also, the spreader tip 60 can be used to apply a sheet 65 of surgical material which is circular in shape with a diameter up to twice the length of the flexible arms 62.

The shaft or push rod 106 has a small diameter in comparision with the deployment tube 102 and the delivery tube 100 and the thin flexible strips 62 of stainless steel provide sufficient space inside the delivery tube 100 to permit a relatively large and thick surgical mesh 65 to be folded over the spreader tip 60 and inserted into the tube 100. For example, each of the flexible strips 62 consists of stainless steel shim stock which is approximately 0.005 inch thick and 0.100 inch wide. Each flexible strip 62 has a finished length of approximately 2.750 inches between the hinge-like connections at its opposite ends.

Referring to FIG. 19, a modified embodiment of the surgical mesh applicator 50 is provided with a pick-up mechanism comprising a wire 200 slidably received inside the hollow push rod 106. The wire 200 extends through the central opening 91 in the tissue manipulating pad 90 and includes a hook 202 at its distal end for engaging the surgical mesh 65. The hook 202 is adapted to snare the surgical mesh 65 against the pad 90 to allow the mesh 65 to be picked up from the abdominal wall and maneuvered into a desired position. For example, the wire 200 comprises a thin hair-like wire spring steel having a curved distal end to provide the hook 202 for engaging the surgical mesh 65. Alternatively, the wire 200 consists of a polymer material which is thermally set or molded to form the hook 202 at its distal end. The wire 200 extends longitudinally along the inside of the push rod 106 and emerges from the proximal end of the push rod 106. An actuator in the form of a push-pull mechanism (not shown) is provided at the proximal end of the surgical mesh applicator 50 to actuate the pick-up wire 200.

In the operation of the embodiment of FIG. 18, the surgical mesh 65 is spread over the opening in the funnel-shaped flange 152 at the proximal end of the delivery tube 100. The spreader tip 60 is placed against the surgical mesh 65 and aligned with the opening in the funnel-shaped flange 152. As shown in FIG. 20, the pick- up wire 200 is initially retracted inside the push rod 106. Then, the pickup wire 200 is advanced distally to advance the hook 202 through the central opening 91 in the tissue manipulating pad 90. As the wire 200 is advanced, the distal end of the wire 200 curves into an arc of predetermined radius to form the hook 202 (FIG. 21). With the tissue manipulating pad 90 flush against the surgical mesh 65, the distal end of the wire 200 passes through the surgical mesh 65 and curves to form the hook 202 which snares the surgical mesh 65. Then, the spreader tip 60 and the push rod 106 are advanced distally into the delivery tube 100 to push the surgical mesh 65 into the delivery tube 100. The applicator 50 is inserted into a trocar or endoscopic tube and aligned with the desired placement site. The surgical mesh 65 is deployed by actuating the delivery flange 122 to expose the spreader tip 60 at the distal end of the delivery tube 102 and by acutating the deloyment flange 130 to expand the spreader tip 60 to spread the mesh 65 over the tissue. Because the surgical mesh 65 is snared by the hook 202, the mesh 65 can be lifted from the tissue by manipulating the applicator 50 and placed in a desired position on the tissue without disengagement from the spreader tip 60. After the surgical mesh 65 is placed in the desired position, the hook 202 can be withdrawn from the surgical mesh 65 by retracting the wire 200 into the hollow push rod 106.

Referring to FIG. 22, in another embodiment of the surgical mesh applicator 50, a solid shaft or push rod 206 is used in place of the hollow push rod or irrigation tube 106 previously described. A delivery button 205 is secured to the proximal end of the shaft 206 in place of the fluid coupling member 105 previously described. Otherwise, the surgical mesh applicator 50 of FIG. 22 includes substantially the same components described above which are identified by the same reference numerals previously used. The embodiment of FIG. 22 is used to apply a non-wetting surgical mesh, e.g., a polypropylene mesh, to internal body tissue.

The invention in its broader aspects is not limited to the specific details of the preferred embodiments shown and described, and those skilled in the art will recognize that the invention can be practiced with modification within the spirit and scope of the appended claims.

We claim:

1. An applicator for applying a spreadable sheet of surgical material to internal body tissue, comprising:
    a delivery tube;
    a deployment tube slidably received within said delivery tube;
    a shaft slidably received within said deployment tube, said shaft having a distal end projecting from the distal end of said deployment tube;
    an expandable spreader tip mounted at the distal end of said shaft and connected to the distal end of said deployment tube for spreading the sheet of surgical material over the tissue, said spreader tip being collapsed when inserted in said delivery tube with said surgical material;
    means for retracting said delivery tube relative to said deployment tube and said shaft to expose said spreader tip and said surgical material at said distal end of said delivery tube;
    first actuator means for urging said spreader tip and surgical material into engagement with the tissue as said deployment tube is retracted; and
    second actuator means for advancing said deployment tube relative to said shaft to expand said spreader tip to apply the surgical material to the tissue.

2. The applicator of claim 1, which includes:
    a return spring for biasing said deployment tube in the proximal direction relative to said shaft to normally maintain said spreader tip collapsed.

3. The applicator of claim 1, wherein said spreader tip comprises:
    a plurality of flexible strips each being pivotally connected at its opposite ends to said distal end of said shaft and to said distal end of said deployment tube, said strips being flexed outwardly when said deployment tube is advanced relative to said shaft to spread the surgical material over the tissue.

4. The applicator of claim 1, wherein:
    said spreader tip includes a plurality of distally extending prongs for engaging the sheet of surgical material to adjust the placement of the surgical material on the tissue.

5. The applicator of claim 1, wherein:
    said deployment tube and said shaft are rotatable together relative to said delivery tube to adjust the angular orientation of said spreader tip and the surgical material.

6. The applicator of claim 5, wherein:
said deployment tube and said shaft are rotatable together when said spreader tip is collapsed inside said delivery tube and when said spreader tip is expanded outside said delivery tube.

7. The applicator of claim 1, which includes:
latch means for latching said delivery tube in a retracted position with said spreader tip and said surgical material exposed at said distal end of said delivery tube.

8. The applicator of claim 7, wherein:
said latch means is operable in any rotational orientation of said deployment tube relative to said delivery tube to latch said delivery tube in the retracted position.

9. The applicator of claim 7, wherein:
said latch means is adapted to permit rotation of said deployment tube and said shaft relative to said delivery tube with said delivery tube latched in the retracted position.

10. The applicator of claim 9, wherein said latch means comprises:
a latching member on said delivery tube; and
a latch ring on said deployment tube adapted to engage said latching member in any rotational orientation of said deployment tube relative to said delivery tube when said delivery tube is moved to the retracted position.

11. The applicator of claim 1, which includes:
detent means for releaseably engaging said deployment tube to retain said spreader tip inside said delivery tube prior to the exposure of said spreader tip therefrom.

12. The applicator of claim 11, wherein:
said detent means is operable in any rotational orientation of said deployment tube relative to said delivery tube to retain said spreader tip inside said delivery tube.

13. The applicator of claim 11, wherein:
said detent means is adapted to permit rotation of said deployment tube and shaft relative to said delivery tube with said spreader tip retained inside said delivery tube.

14. The applicator of claim 13, wherein said detent means comprises:
a latching member on said delivery tube; and
an annular groove on said deployment tube adapted to engage said latching member in any rotational orientation of said deployment tube relative to said delivery tube when said spreader tip is retracted.

15. The applicator of claim 1, which includes:
a hollow funnel-shaped flange at the proximal end of said delivery tube for guiding said spreader tip and the surgical material into said delivery tube.

16. The applicator of claim 1, wherein:
said shaft comprises an irrigation tube for supplying fluid to the sheet of surgical material.

17. The applicator of claim 16, which includes:
a nozzle at the distal end of said irrigation tube for discharging the fluid therefrom.

18. The applicator of claim 17, wherein:
said nozzle includes a plurality of distally extending prongs for engaging the sheet of surgical material to adjust the placement of the surgical material on the tissue.

19. The applicator of claim 1, which includes:
a pick-up mechanism for securing the sheet of surgical material to said spreader tip.

20. The applicator of claim 19, wherein:
said pickup mechanism comprises a wire slidably mounted on said spreader tip and provided with a hook for engaging the surgical material to snare the surgical material on said spreader tip.

21. An endoscopic applicator for insertion into an endoscopic tube for applying a sheet of surgical material to internal body tissue, comprising:
a delivery tube sized for insertion into the endoscopic tube;
a deployment tube slidably received within said delivery tube;
a shaft slidably received within said deployment tube, said shaft having a distal end projecting from the distal end of said deployment tube;
an expandable spreader tip mounted at the distal end of said shaft and connected to the distal end of said deployment tube for spreading the sheet of surgical material over the tissue, said spreader tip being collapsed when inserted in said delivery tube with said surgical material;
a finger grip on said delivery tube for retracting said delivery tube relative to said deployment tube and said shaft to expose said spreader tip and said surgical material at said distal end of said delivery tube;
a first actuator on said deployment tube for applying pressure to said shaft to urge said spreader tip into engagement with the tissue as said deployment tube is retracted; and
a second actuator on said deployment tube for advancing said deployment tube relative to said shaft to expand said spreader tip to apply the surgical material to the tissue.

22. The applicator of claim 21, which includes:
a return spring within said deployment tube for biasing said deployment tube in the proximal direction relative to said shaft to normally maintain said spreader tip collapsed.

23. The applicator of claim 21, wherein said spreader tip comprises:
a plurality of flexible strips each being pivotally connected at its opposite ends to said distal end of said shaft and to said distal end of said deployment tube, said strips being flexed outwardly when said deployment tube is advanced relative to said shaft to spread the surgical material over the tissue.

24. The applicator of claim 21, wherein:
said spreader tip includes a plurality of distally extending prongs for engaging the sheet of surgical material to adjust the placement of the surgical material on the tissue.

25. The applicator of claim 21, wherein:
said deployment tube and said shaft are rotatable together relative to said delivery tube to adjust the angular orientation of said spreader tip and the surgical material.

26. The applicator of claim 25, wherein:
said deployment tube and said shaft are rotatable together when said spreader tip is collapsed inside said delivery tube and when said spreader tip is expanded outside said delivery tube.

27. The applicator of claim 21, which includes:
latch means for latching said delivery tube in a retracted position with said spreader tip and said surgical material exposed at said distal end of said delivery tube.

28. The applicator of claim 27, wherein:
said latch means is operable in any rotational orientation of said deployment tube relative to said delivery tube to latch said delivery tube in the retracted position.

29. The applicator of claim 27, wherein:
said latch means is adapted to permit rotation of said deployment tube and said shaft relative to said delivery tube with said delivery tube latched in the retracted position.

30. The applicator of claim 29, wherein said latch means comprises:
a latching member on said delivery tube; and
a latch ring on said deployment tube adapted to engage said latching member in any rotational orientation of said deployment tube relative to said delivery tube when said delivery tube is moved to the retracted position.

31. The applicator of claim 21, which includes:
detent means for releaseably engaging said deployment tube to retain said spreader tip inside said delivery tube prior to the exposure of said spreader tip therefrom.

32. The applicator of claim 31, wherein:
said detent means is operable in any rotational orientation of said deployment tube relative to said delivery tube to retain said spreader tip inside said delivery tube.

33. The applicator of claim 31, wherein:
said detent means is adapted to permit rotation of said deployment tube and shaft relative to said delivery tube with said spreader tip retained inside said delivery tube.

34. The applicator of claim 33, wherein said detent means comprises:
a latching member on said delivery tube; and
an annular groove on said deployment tube adapted to engage said latching member in any rotational orientation of said deployment tube relative to said said delivery tube when said spreader tip is retracted.

35. The applicator of claim 21, which includes:
a hollow funnel-shaped flange at the proximal end of said delivery tube for guiding said spreader tip and the surgical material into said delivery tube.

36. The applicator of claim 21, wherein:
said shaft comprises an irrigation tube for supplying fluid to the sheet of surgical material.

37. The applicator of claim 36, which includes:
a nozzle at the distal end of said irrigation tube for discharging the fluid therefrom.

38. The applicator of claim 37, wherein:
said nozzle includes a plurality of distally extending prongs for engaging the sheet of surgical material to adjust the placement of the surgical material on the tissue.

39. The applicator of claim 21, which includes:
a pick-up mechanism for securing the sheet of surgical material to said spreader tip.

40. The applicator of claim 39, wherein:
said pickup mechanism comprises a wire slidably mounted on said spreader tip and provided with a hook for engaging the surgical material to snare the surgical material on said spreader tip.

* * * * *